United States Patent
Shelton et al.

(10) Patent No.: US 11,213,190 B2
(45) Date of Patent: Jan. 4, 2022

(54) ENDOSCOPE WORKING CHANNEL PROTECTION

(71) Applicant: GYRUS ACMI, INC., Southborough, MA (US)

(72) Inventors: Kurt Shelton, Bedford, MA (US); Allison Dianis, Andover, MA (US); Giorgio Brusa, Needham, MA (US)

(73) Assignee: Gyrus Acmi, Inc., Westborough, MA (US)

( * ) Notice: Subject to any disclaimer, the term of this patent is extended or adjusted under 35 U.S.C. 154(b) by 453 days.

(21) Appl. No.: 16/094,915

(22) PCT Filed: Jun. 2, 2016

(86) PCT No.: PCT/US2016/035434
§ 371 (c)(1),
(2) Date: Oct. 19, 2018

(87) PCT Pub. No.: WO2017/209754
PCT Pub. Date: Dec. 7, 2017

(65) Prior Publication Data
US 2019/0090727 A1   Mar. 28, 2019

(51) Int. Cl.
*A61B 1/00*        (2006.01)
*A61B 1/018*       (2006.01)
(Continued)

(52) U.S. Cl.
CPC .......... *A61B 1/018* (2013.01); *A61B 1/00071* (2013.01); *A61B 1/00131* (2013.01);
(Continued)

(58) Field of Classification Search
None
See application file for complete search history.

(56) References Cited

U.S. PATENT DOCUMENTS 5,374,261 A    12/1994 Yoon
5,549,601 A *  8/1996 McIntyre ............... A61B 18/24
                                              600/108
(Continued)

FOREIGN PATENT DOCUMENTS

CN   204203483 U   3/2015
CN   105338879 A   2/2016
(Continued)

OTHER PUBLICATIONS

International Search Report and Written Opinion for International Application PCT/US2016/035434, dated Jan. 30, 2017.
(Continued)

*Primary Examiner* — Timothy J Neal
(74) *Attorney, Agent, or Firm* — Schwegman Lundberg & Woessner, P.A.

(57) ABSTRACT

An endoscope including an insertion tube, a working, channel located within the insertion tube, and a protecting feature disposed within at least a portion, of the working channel The protecting feature may be adapted to protect the working-channel from thermal damage and/or from mechanical damage caused by a medical instrument located in the working channel. The protecting feature may be adapted to determine presence or absence of a medical instrument within the working channel, arid/or a location of the medical instrument within the working channel.

20 Claims, 4 Drawing Sheets

(51) Int. Cl.
*A61B 1/313* (2006.01)
*A61B 18/00* (2006.01)
*A61B 18/12* (2006.01)

(52) U.S. Cl.
CPC ............ *A61B 1/3132* (2013.01); *A61B 18/00* (2013.01); *A61B 18/12* (2013.01)

(56) References Cited

U.S. PATENT DOCUMENTS

| | | | |
|---|---|---|---|
| 5,702,344 A | 12/1997 | Silverstein | |
| 6,056,735 A * | 5/2000 | Okada | A61B 17/320092 606/1 |
| 7,569,626 B2 | 8/2009 | Truckai | |
| 8,870,761 B2 | 10/2014 | Vayser et al. | |
| 2006/0206178 A1 | 9/2006 | Kim | |
| 2007/0033379 A1 | 2/2007 | Kirsch | |
| 2008/0015409 A1* | 1/2008 | Barlow | A61B 18/1492 600/106 |
| 2008/0144515 A1 | 6/2008 | Ouellette et al. | |
| 2010/0087705 A1 | 4/2010 | Byers et al. | |
| 2010/0145142 A1 | 6/2010 | Begemann et al. | |
| 2010/0152538 A1* | 6/2010 | Gleason | A61B 1/00055 600/117 |
| 2011/0213349 A1 | 9/2011 | Brown | |
| 2013/0072753 A1* | 3/2013 | Zappia | A61B 5/06 600/108 |
| 2014/0350564 A1 | 11/2014 | Huszar et al. | |
| 2015/0366610 A1* | 12/2015 | Tsuruta | A61B 18/1492 606/46 |

FOREIGN PATENT DOCUMENTS

| | | |
|---|---|---|
| CN | 105358036 A | 2/2016 |
| CN | 109310289 A | 2/2019 |
| EP | 1723899 A1 | 11/2006 |
| EP | 3439530 A1 | 2/2019 |
| JP | H01249031 A | 10/1989 |
| JP | H10262900 A | 10/1998 |
| JP | H11244223 A | 9/1999 |
| JP | 2000237127 A | 9/2000 |
| JP | 2001231746 A | 8/2001 |
| JP | 2002085334 A | 3/2002 |
| JP | 2005080983 A | 3/2005 |
| JP | 2005318982 A | 11/2005 |
| JP | 2007282882 A | 11/2007 |
| JP | 2010042139 A | 2/2010 |
| JP | 2010214121 A | 9/2010 |
| JP | 2012143391 A | 8/2012 |
| JP | 2019516480 A | 6/2019 |
| JP | 6806798 B2 | 12/2020 |
| JP | 2021045590 A | 3/2021 |
| WO | 2008/144515 A1 | 11/2008 |
| WO | 2010/053575 A2 | 5/2010 |
| WO | WO-2015068863 A1 | 5/2015 |
| WO | WO-2015194317 A1 | 12/2015 |
| WO | WO-2017209754 A1 | 12/2017 |

OTHER PUBLICATIONS

"Chinese Application Serial No. 201680085918.8, Office Action dated Aug. 3, 2020", w/English Translation, 19 pgs.
"European Application Serial No. 16729726.6, Communication Pursuant to Article 94(3) EPC dated Oct. 23, 2020", 5 pgs.
"Japanese Application Serial No. 2018-560465, Office Action dated May 12, 2020", w/ English Translation, 10 pgs.
"Japanese Application Serial No. 2018-560465, Response filed Aug. 7, 20 to Office Action dated May 12, 2020", w/ English Claims, 7 pgs.
"Chinese Application Serial No. 201680085918.8, Response filed Nov. 23, 2020 to Office Action dated Aug. 3, 2020", w/English Claims, 28 pgs.
"European Application Serial No. 16729726.6, Response to Communication pursuant to Rules 161(1) and 162 EPC filed Apr. 9, 2019", 20 pgs.
"International Application Serial No. PCT/US2016/035434, International Preliminary Report on Patentability dated Dec. 13, 2018", 8 pgs.
"Japanese Application Serial No. 2018-560465, Office Action dated Oct. 29, 2019", W/English Translation. 8 pgs.
"Japanese Application Serial No. 2018-560465, Response filed Jan. 27, 2020 to Office Action dated Oct. 29, 2019", w/ English Claims, 7 pgs.
"Chinese Application Serial No. 201680085918.8, Office Action dated Mar. 23, 2021", w/English Translation, 22 pgs.
"Chinese Application Serial No. 201680085918.8, Office Action dated Jul. 1, 2021", w/English Translation, 21 pgs.
"Chinese Application Serial No. 201680085918.8, Response filed Jun. 1, 21 to Office Action dated Mar. 23, 2021", w/o English Claims, 7 pgs.
"European Application Serial No. 16729726.6, Response filed Feb. 22, 2021 to Communication Pursuant to Article 94(3) EPC dated Oct. 23, 2020", 3 pgs.
"Chinese Application Serial No. 201680085918.8, Response filed Sep. 15, 2021 to Office Action dated Jul. 1, 2021", with English claims, 17 pgs.
"Japanese Application Serial No. 2020-201525, Notification of Reasons for Rejection dated Nov. 9, 2021", with English translation, 6 pgs.

* cited by examiner

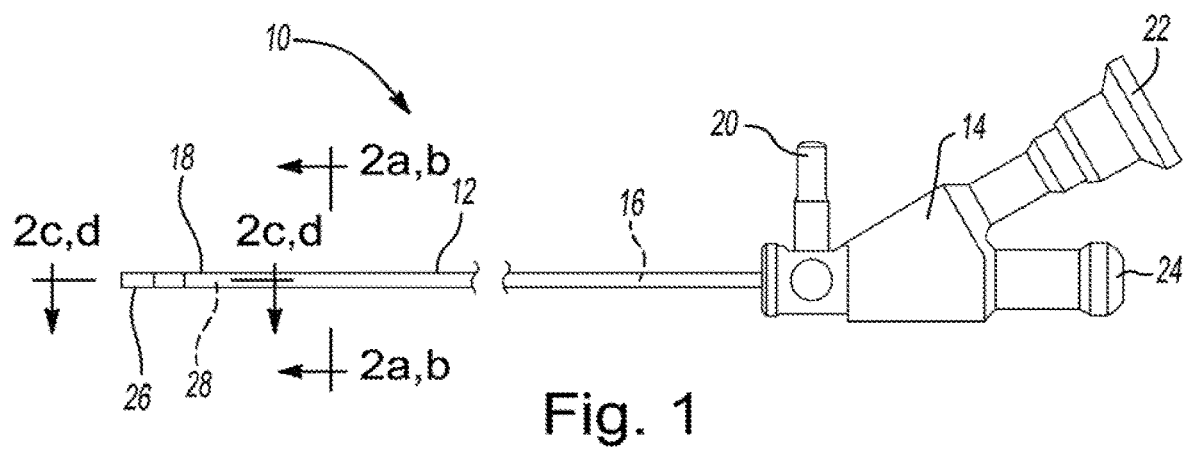
Fig. 1
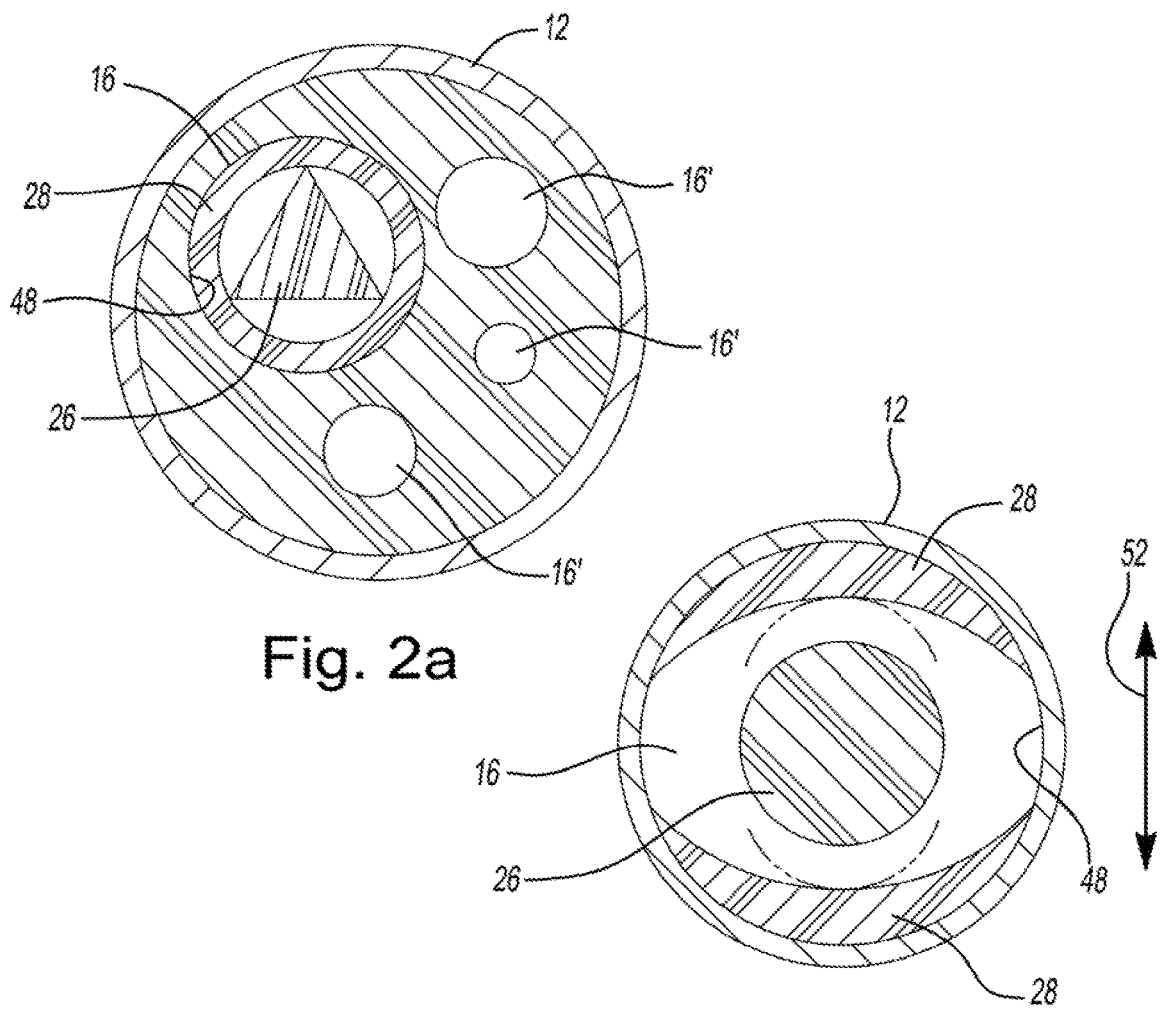
Fig. 2a
Fig. 2b

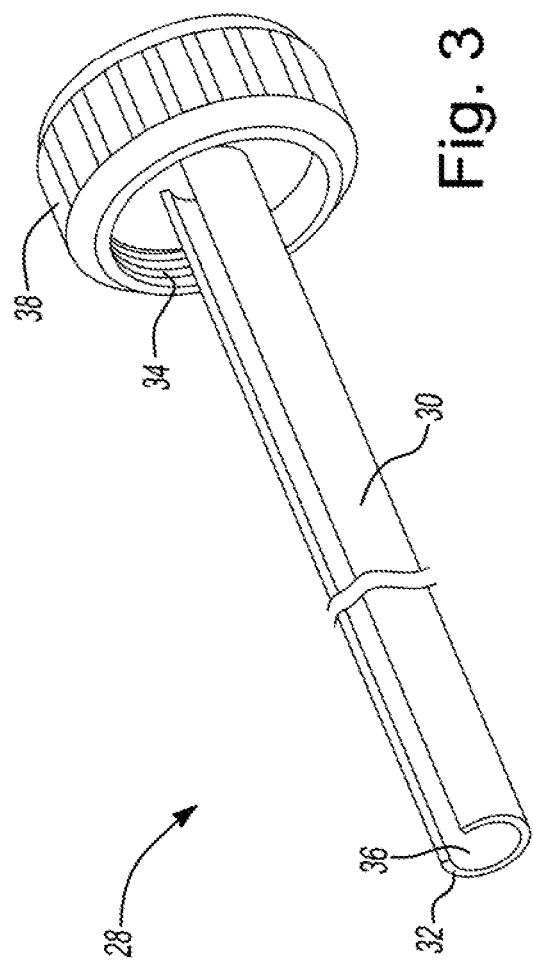
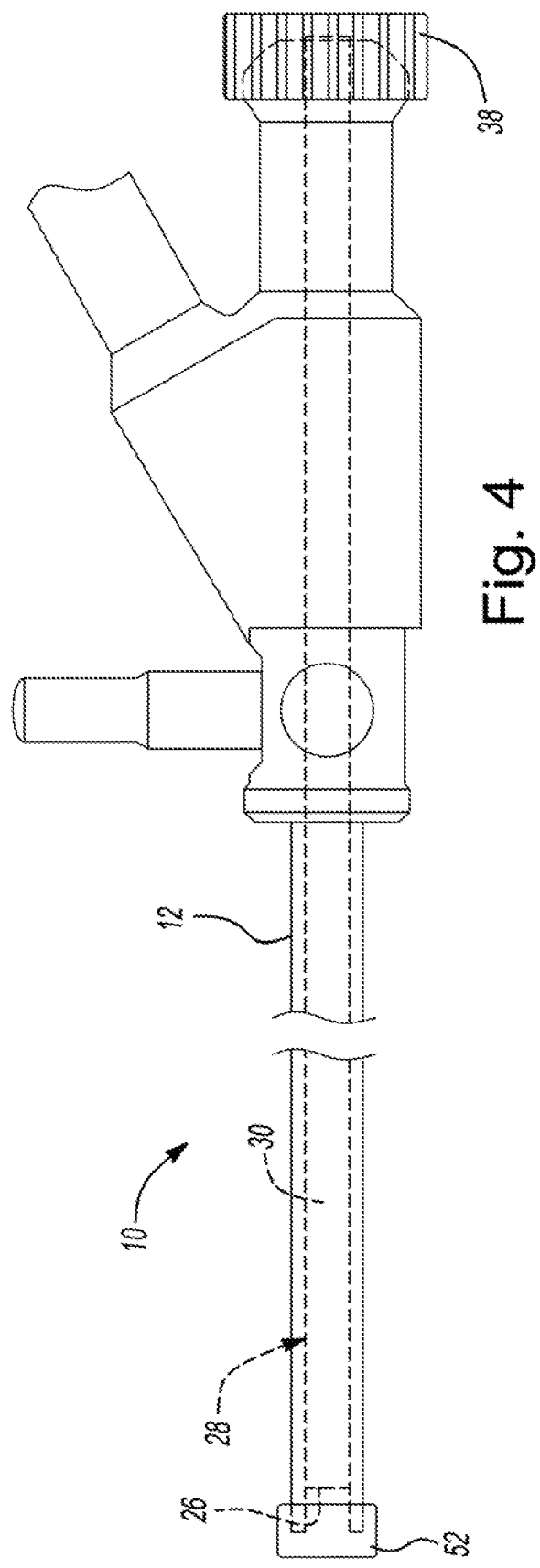

ENDOSCOPE WORKING CHANNEL
PROTECTION

FIELD

These teachings relate generally to an endoscope. More particularly, these teachings provide protecting features for an endoscope working channel.

BACKGROUND

An endoscope is a medical device that can be used in various medical procedures, such as endoscopic surgery. An endoscope generally includes a hand piece and an insertion tube extending from the hand piece. The insertion tube includes one or more working channels. During a medical procedure involving an endoscope, the insertion tube is passed through an orifice or incision in the anatomy and steered to a site of interest in the anatomy. Various endoscopic instruments can be passed through the one or more working channels and directed to the site of interest to carry out the medical procedure. The endoscopic instruments may include, for example, various illuminating devices, cameras, dissectors, graspers, retractors, scissors, needles, baskets, cautery instruments, forceps, lasers, and the like.

While passing an endoscopic instrument through the one or more working channels, contact between the instrument and the inner walls or surfaces of the working channel may scratch, gouge, dent, and/or otherwise cause damage to the working channel. This may be exacerbated when the insertion tube is in a bent state, and the endoscopic instrument is moved, reciprocated, articulated, and/or otherwise operated therein. Scratching, gouging, and/or denting of the working channel, may cause shavings and/or debris to separate from the working channel, which may undesirably contaminate the anatomy, a sample separated from the anatomy, and/or reduce the lifespan of the insertion tube, endoscope, or both.

In other instances, the working channel or insertion tube may be damaged when an instrument such as laser is prematurely operated or fired when the laser is not fully inserted through the working channel. More specifically, thermal damage to the working channel or insertion tube may occur when the laser is at a location in the working channel where upon firing a laser wavelength from the laser, the laser wavelength contacts the working channel before exiting the insertion tube. Such thermal damage may render the insertion tube inoperable or at least severely limit its lifespan. Moreover, laser wavelength contact with the working channel may weaken or affect the strength and efficacy of the laser wavelength.

In view of these shortcomings, it may be desirable to have one or more protecting features to protect one or more working channels of an insertion tube of an endoscope. It may be desirable to have one or more protecting features to protect the one or more working channels of the insertion tube from mechanical and/or thermal damage caused by moving, reciprocating, and/or otherwise operating one or more endoscopic instruments therein. It may be desirable to have one or more protecting features to reduce, minimize, prevent, or eliminate wear and damage to the one or more working channels and/or insertion tube caused by an endoscopic instrument being passed through or operated in the working channel. It may be desirable to reduce or minimize wear and damage to an insertion tube and/or working channel in order to extend the lifespan of an insertion tube and/or prevent debris, shavings, and the like from separating from the working channel and contaminating the anatomy and/or a tissue sample obtained from the anatomy. It may be desirable to have one or more protecting features that can assist in monitoring and/or determining a location or position of one or more endoscopic instruments in the one or more working channels, and prevent operation of the endoscopic instrument when the endoscopic instrument is not in a preferred location in the working channel. Various endoscopes and endoscopic instruments are known, including those disclosed in WO2011133941A3, WO2007033379A3, US 20140350564, US20060206178A1, U.S. Pat. Nos. 8,870,761, and 7,569,626, which are all incorporated by reference herein for all purposes.

SUMMARY

One or more protecting features for one or more endoscope working channels are provided. The teachings contemplate one or more protecting features that may protect the working channel of the insertion tube from mechanical and/or thermal damage or any other type of wear or damage caused by moving, reciprocating, and/or otherwise operating an endoscopic instrument in the working channel. Advantageously, these teachings may reduce or minimize wear and/or damage to an insertion tube and/or working channel so that the life of the insertion tube and/or endoscope is extended. Advantageously, these teachings may reduce or minimize contamination of the anatomy and or samples removed from the anatomy. These teachings also provide one or more protecting features that can assist in monitoring and/or determining a location or position of an endoscopic instrument in the working channel, and prevent operation of the endoscopic instrument when the endoscopic instrument is not in a preferred or desired location in the working channel.

BRIEF DESCRIPTION OF THE DRAWINGS

FIG. 1 is a side view of a medical device.
FIG. 2a is a cross-sectional view of an insertion tube of FIG. 1.
FIG. 2b is a cross-sectional view of an insertion tube of FIG. 1.
FIG. 3 is a perspective view of a sleeve for use with a medical device.
FIG. 4 is a side view of a medical device.

DETAILED DESCRIPTION

Figure 2C:
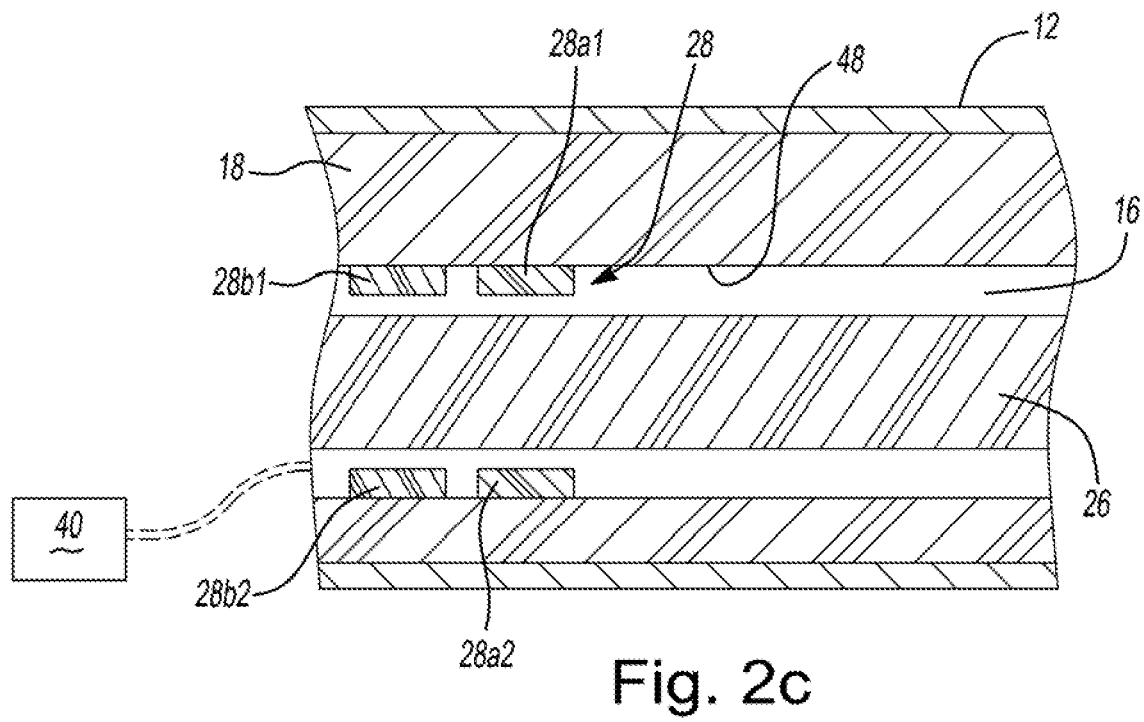
FIG. 2c is a cross-sectional view of an insertion tube of FIG. 1.

These teachings relate to a medical device. The medical device may be any device that may function to provide a user with visual access into a location of interest in the anatomy of a patient. The medical device may function to provide for an instrument such as an endoscopic instrument to be inserted into a remote location, such as a site of interest in the anatomy of a patient. The medical device can be used in virtually any medical procedure. For example, the medical device can be used in minimally-invasive procedures, such as percutaneous nephrolithotomy (PCNL). The medical device may be as endoscope. The medical device may be any endoscope, such as a cystoscope, as nephroscope, a bronchoscope, a laryneoscope, an otoscope, an arthroscope, a laparoscope, or a combination thereof.

The medical device may include a hand piece. The hand piece may function to provide an area for a user to grip, hold, manipulate, and/or operate the medical device. The hand piece may include one or more controls so that a user can move, manipulate, and/otherwise operate the medical device, the insertion tube, the one or more medical instruments inserted into the insertion tube, or a combination thereof. For example, the one or more controls may cause at least a portion of the insertion tube (e.g., a distal bending portion) to bend or articulate.

The hand piece may include one or mores, ports. The one or more ports may include one or more working channel ports. The one or more ports may function to provide access into the one or more working channels of the insertion tube. For example, one or more ports may provide irrigation fluid, suction, and/or one or more medical instruments to be supplied to the one or more working channels and ultimately to a site of interest in the anatomy.

The medical device may include an insertion tube. The insertion tube may function to provide for at least a portion of the medical device to be inserted into a patient or the anatomy, while a portion of the medical device remains outside of the patient or anatomy (e.g., the hand piece). The insertion tube may be an elongated, tubular member that extends along a longitudinal axis between opposing proximal and distal ends. The proximal end of the insertion tube may be connected to the hand piece. During a medical procedure, the distal end may be inserted into a patient or the anatomy. The insertion tube may be substantially straight; may include one or more angles, bends or arcs; or a combination thereof. The insertion tube may be substantially rigid; substantially flexible; substantially resilient; or a combination thereof. For example, at least a distal portion of the insertion tube may be moveable, articulable, bendable, deflectable, and/or steerable so that a user can steer at least the distal portion around features in the anatomy to a site of interest.

The insertion tube may include one or more working channels. The one or more working channels may function to provide for one or more medical instruments to be inserted into and passed through the insertion tube. The one or more working channels may be defined by one or more discrete or individual lumen or channels in the insertion tube. The one or more working channels may have the same size, or the sizes can vary to accommodate different sized medical instruments. The one or more medical instruments can be passed through discrete or individual lumen or channels in the insertion tube, or a plurality of medical instruments can be passed through a single lumen or channel. The working channel may include Teflon. Without one or more of the protecting features disclosed herein, inserting, removing, manipulating, articulating, using, activating, tiring, and/or otherwise using one or more medical instruments within the working channel may undesirably subject the inner walls or surfaces of the one or more working channels, and/or the Teflon to damage, such as thermal damage and/or mechanical damage.

The working channel may include an inner wall or surface. In some instances, the inner wall or surface of the working channel may be the same as the inner wall or surface of the insertion tube (See e.g., FIG. 2b). In some instances, the inner wall or surface of the working channel may be located within the insertion tube and be different than an inner wall or surface of the insertion tube, which may be the case when the insertion tube includes a plurality of working channels (See e.g., FIG. 2a). In some instances, at least a portion of the inner wall or surface of the working channel may be the same as the inner wall or surface of the insertion tube and another portion of the inner wall or surface of the working channel may be discrete from the inner wall or surface of the insertion tube (See e.g., FIG. 2c).

One or more medical instruments can be inserted into and/or passed through the medical device, the insertion tube, the one or more working channels in the insertion tube, or a combination thereof. For example, the one or more medical instruments may be any suitable instruments used to: look more closely at an area inside the anatomy; obtain and remove tissue samples; treat certain diseases; remove tumors; stop bleeding; or break down foreign bodies, or a combination thereof. The one or more medical instruments may be one or more endoscopic instruments. The one or more medical instruments may include irrigation fluid, suction, or both. The one or more medical instruments may include one or more catheters, needles, forceps, cautery instruments, lithotripters, lasers, retractors, graspers, dissectors, basket devices, scissors, cameras, light sources, the like, or a combination thereof. The one or more medical instruments may be controlled by the user, with one or more controls located on the hand piece, and/or one or more controls located at a remote location, such as a foot pedal, for example.

The medical device may include one or more stoppers. The one or more stoppers may function to support one or more medical instruments, protecting devices, sleeves, or a combination thereof within an insertion tube and/or working channel. The one or more stoppers may function to prevent one or more medical instruments, protecting devices, sleeves, or a combination from moving, sliding, and/or being inadvertently repositioned or moved in the insertion tube and/or working channel. The one or more stoppers may be made at least partially of an elastic or rubber material. The one or more stoppers may be an electrical insulator. The one or more stoppers may be an O-ring. The one or more stoppers may be permanently attached to an inner wall or surface of a working channel, insertion tube, or both. The one or more stoppers may be removable or replaceable so that different size and/or shaped stopper can be selectively installed depending on the medical instrument provided into a working channel. The one or more stoppers may be movable and/or static relative to the insertion tube, working channel, or both. The one or more stoppers may extend short of a distal end of an insertion tube, working channel, or both; extend proud of the distal end of the insertion tube, working channel, or both; or be flush with a distal end of the insertion tube, working channel, or both.

The medical device may include one or more protecting features. The one or more protecting features may function to protect and/or provide protection to the one or more working channels, the insertion tube, the endoscope, or a combination thereof. The one or more protecting features may function to restrict or prevent contact between the working channel and the one or more medical instruments inserted into the working, channel. The one or more protecting features may function to restrict or prevent damage to the working channel and/or to the interior of the insertion tube when one or more medical instruments are operated in the one or more working channels. Operated may mean when the medical instrument is inserted, moved, manipulated, oriented, rotated, pushed, pulled, articulated, actuated, operated, fired, the like, or a combination thereof within the working channel. The one or more protecting features may function to restrict, reduce, or prevent damage to the working channel and/or interior of the insertion tube in the form of scratching, gouging, denting, deforming, trauma, when the one or more medical instruments are inserted, moved, manipulated, oriented, rotated, pushed, pulled, articulated, or a combination thereof in the working channel. The one or more protecting features may function to restrict, reduce, or prevent removal of debris, shavings, and/or fragments from the working channel when the one or more medical instruments contact the working channel. The one or more protecting features may function to restrict or prevent metal to metal contact between the working channel and the one or more medical instruments into the working channel. The one or more protecting features may function to add strength to the insertion tube, the working channel, or both. The one or more protecting features may function to add strength to the insertion tube, the working channel, or both especially in the areas where the insertion tube is bendable, deflectable, articulable, and/or deformable, which may be at least the distal region or portion of the insertion tube. The one or more protecting features may function to provide a logic check to determine a position or location of one or more medical instruments in the one or more working channels and/or insertion tube relative to a known, fixed, or determined location, such as the hand piece, a patient, the insertion tube, a proximal end of the insertion tube, a distal end of the insertion tube, or a combination thereof. The one or more protecting features may function to detect presence or absence of a medical instrument in the insertion tube. The one or more protecting features may function to ensure that a medical instrument is fully inserted through the insertion tube and/or extends out of a distal end of the insertion tube.

The one or more protecting features may include any one or more of the features, functions, and properties of protecting features described herein. For example, a protecting feature may include a combination of one or more protecting segments illustrated in FIG. 2c, one or more cut outs illustrated in FIG. 3, and/or one or more pairs of capacitors illustrated in FIG. 2b, etc.

The protecting feature may be located along an entire length of the working channel, or only along portion thereof. For example, a protecting feature may be located at a proximal region of the working channel, a distal region of the working channel, or a central region of the working channel. In some instances, it may be advantageous for the protecting feature to extend along an entire length of the working channel or insertion tube so that damage to the inner wall or diameter of the insertion tube or working channel is prevented. This may be especially desirable when the medical instrument is a laser. That is, it is known that the outermost cover or sheathing of a laser can become damaged or comprised anywhere along its length, and when the laser is fired, the laser wavelength can be emitted from the damaged or compromised area. Thus, if the protecting feature is located alone an entire length of the working channel or insertion tube, damage to the insertion tube, working channel and/or medical device can be reduced or prevented. A protecting feature located at a distal portion or region may be desirable when the distal portion or region is bendable in order to strengthen the distal region so that the insertion tube can withstand repeated manipulation, bending, articulation, and/or deflection of the insertion tube while one or more medical instruments are moved, rotated, bent, reciprocated, the like, and/or otherwise operated therein. The protecting feature may be located along the bending regions, angles, or directions of the insertion tube and/or working channel so that the protecting features function to strengthen the insertion tube when the insertion tube and/or working channel is subjected to extreme bending as may be the ease when accessing a site of interest, such as a lower pole of a kidney, for example.

The protecting feature may be made of a suitable material. The material of the protecting feature may be such that the protecting feature is highly absorbent to laser wavelengths and/or has a high thermal conductivity. The material may have a thermal conductivity in the range of 1 to 20 W/mK. The material of the protecting feature may be such that a laser thermal energy is unable to penetrate the protecting feature and is thus unable to break or compromise the working channel, the insertion portion, or both. The material of the protecting feature may be such that the protecting feature is flexible, kink resistant, and laser safe. The material of the protecting feature may be such that the protecting feature can withstand scratching, gouging, denting, and/or deformation when one or more medical instruments contact the protecting feature. For example, the protecting feature may be made from a plastic or non-metal, such as polytetrafluoroethylene (PTFE), polyethylene, high density polyethylene, high molecular weight polyethylene, or other thermal polymer. For example, the protecting feature may be made from a material that has a high water content since it is known that water can absorb laser light. For example, the protecting feature may be made from a metal oxide, diamond, diamond crystals, boron nitride, aluminum nitride, carbon boron nitride, or carbon nanotubes. For example, the protecting feature may comprise a polymer that is in fused with an additive such as metal oxide, or diamond, diamond crystals, boron nitride, aluminum nitride, carbon boron nitride, or carbon nanotubes. For example, the protecting feature may comprise a thermal polymer that is cross-linked. For example, the protecting feature may be a high electron density material to block light. For example, the protecting feature may include a radiopaque element or a radio-opacifier to stop photon absorption. For example, the protecting layer may have a high thermal resistance and be highly thermally conductive in order to dissipate the energy that does get absorbed. For example, the protecting feature may be formed by low pressure vapor deposition or low temperature vapor deposition to apply or fuse the protecting feature to the working channel.

The protecting feature may be a layer of one or more materials or features located within the working channel. The protecting feature may be connected to an inner wall or surface of the one or more of the working channels, an inner wall or surface of the insertion tubes, or both. The connection may be removable or permanent. For example, the protecting feature may be such that it can be removed or replaced. This may be advantageous when the insertion tube can be autoclaved and reused, but the protecting features need to be replaced as a result of damage. This may also be advantageous when different sizes or types of protecting features are desired to be used. For example, one particular protecting feature may be desired when using a certain medical instrument, such as a forceps, while another type of protecting feature may be desired when using a laser. Accordingly, a removable connection may provide a user with unlimited flexibility while still using a single or standard insertion tip.

The protecting feature may be or include one or more capacitors. The protecting feature may be or include one or more parallel plate capacitors. Preferably, the protecting feature includes at least one pair of opposing parallel plate capacitors. However, two or more opposing parallel plate capacitors may be preferred. The one or more capacitors may function to provide a logic check to determine a position or location of one or more medical instruments in the one or more working channels relative to a known, fixed, or determined location, such as the hand piece, a patient, the insertion tube, a proximal end of the insertion tube, a distal end of the insertion tube, or a combination thereof. The logic check may be performed by the medical device, a controller in communication with the medical device, or a computer in communication with the medical, device. The one or more capacitors may function to detect presence or absence of a medical instrument in the insertion tube. The one or more capacitors may function to ensure that a medical instrument is fully inserted through the insertion tube and/or extends out of a distal end of the insertion tube. If the medical instrument is a laser, ensuring that the laser is fully inserted through the insertion tube and/or extends out of a distal end of the insertion tube may be desirable such that when the laser is activated and/or fired, the laser wavelengths do not contact the working channel and/or an inner portion of the insertion tube so that unnecessary damage to the medical device and/or insertion tube can be prevented. If the logic check determines that the medical instrument is not in a desired location or position, the medical instrument may be prevented from being operated or fired if the medical instrument is a laser. Accordingly, accidental or premium firing can be restricted or prevented.

The protecting feature (e.g., capacitors) can be operated according to a method. When capacitors oppose one another without a medical instrument located in between, a first capacitance between the capacitors can be measured or determined by a controller or logic system. When a medical instrument is located between the capacitors, a second capacitance between the capacitors can be measured or determined by the controller or logic system. The second capacitance can be a predetermined value or working range, or the second capacitance can be a value that does not equal the first capacitance. The controller, logic system, medical device, and/or medical instrument can be adapted, configured, or operated such that when the second capacitance is measured or determined by the controller or logic system, the medical instrument can be operated. Alternatively, when the second capacitance is not measured or determined by the controller or logic system, the medical instrument can be restricted or prevented from being operated.

Any number of such opposing capacitors can be used. For example, two sets of opposing capacitors can be used. For example, a proximal pair of capacitors and a distal pair of capacitors can be arranged in the working channel. When a medical instrument is not located within the working channel, and/or is located proximal to both pairs of capacitors, the capacitance between each of the first pair and the second pair of opposing capacitors can be C1 and C2, respectively determined by the controller or logic system. When the medical instrument is located in between the tint pair of capacitors, the capacitance between the first pair of capacitors may be determined by the controller or logic system to be C1'. C1' may be a measured value or working range, or may be a value that does not equal C1 or an acceptable working range of C1. When the controller or logic system reads that the capacitances as C1' and C2, the controller or logic system understands that the medical instrument is located or positioned somewhere between the first and second pair of capacitors. The controller or logic system may restrict or prevent operation of the medical instrument during this time. As the medical instrument is further moved so that it is located or positioned between both pairs of capacitors, the controller or logic system may determine the capacitance to be C1' and C2' and thus knows that that the medical instrument is located between both pairs of capacitors. C2' may be a measured value or working range, or may be a value that does not equal C2 or an acceptable working range of C2. By arranging the capacitors near a distal end of the working tube, the capacitors can be used to determine the presence, absence, location and/or position of a distal end or portion of the medical instrument relative to the hand piece, a distal end of the insertion tube, or both. Accordingly, a medical instrument can be allowed to operate or restricted from operating depending on its presence, location, and/or position in the insertion tube.

The protecting feature may include a material that is at least partially reflective. If the medical instrument is a laser, during use the laser may be actuated to send a test signal or wavelength, which may be a laser wavelength that is shorter than a normal wavelength used during a medical procedure. If the laser is not properly located in the working channel (for example, if the laser does not extend past the distal end of the insertion tube), the reflective surface may function to create scattering of the test signal or wavelength or some other pattern that can be detected by the medical device, a controller, or both to indicate that the laser is not properly positioned and thus prevent the laser from activating or firing a normal signal or wavelength. In addition, or alternatively, if a covering or sheath of the laser is compromised (e.g., torn), firing the test signal or wavelength may cause the test signal or wavelength to exit the laser somewhere along its length even if the distal end of the laser is properly positioned relative to the distal end of the insertion tube. Accordingly, the reflective surface may function to create scattering of the test signal or wavelength or some other pattern that can be detected by the medical device, a controller, or both to and thus prevent the laser from firing a normal signal or wavelength thus preventing damage to the interior or working channel of the insertion tube.

The protecting feature may include one or more protecting segments. The one or more protecting segments may be disposed within a least a portion of the working channel and may function to allow the insertion tube and/or the one or more medical instruments to bend, flex, and articulate. The one or more protecting segments may extend at least partially around a circumference of the working channel, but in some instances it may be preferred that the segments extend completely around the circumference of a working channel. The one or more protecting segments may extend at least partially around a circumference of the working channel in one or more sections relative to a longitudinal axis of the insertion tube. For example, the one or more segments may be arranged parallel to the longitudinal axis and spaced apart about 20 degrees or so apart, about 30 degrees or so apart, about 45 degrees or so apart, about 90 degrees or so apart, about 135 degrees or so apart, or even about 180 or so degrees apart. Alternatively, the segments can be irregularly spaced apart. Alternatively, the segments can be helically or randomly arranged around an interior of the one or more working channels. The one or more protecting segments may be partially connected and partially free from any connections. For example, an end of a protecting segment may be connected to the working channel or an adjacent protecting segment, while an opposing end is free of any connections. One skilled in the art may correlate such a description to snake skin, snake scales, and or roofing shingles. In this regard, when the insertion tube is bent, articulated, and/or moved, the working channel would remain covered and protected by the one or more protecting segments.

The protecting feature may be used as part of a sleeve so that the protecting feature can be quickly and easily removed or separated from the medical device and/or insertion tube. When used as part of a sleeve, the protecting feature may include an elongated portion that includes any of the functional, material and/or structural characteristics described herein. As was discussed above, a removable protecting feature may be advantageous when the insertion tube can be autoclaved and reused, but the protecting features need to be replaced as a result of damage. This may also be advantageous when different sizes or types of protecting features are desired to be used. For example, one particular protecting feature may be desired when using a certain medical instrument, such as forceps, while another type of protecting feature may be desired when using a laser.

The protecting feature or elongated portion may include a cut out. The cut out may function to provide an opening to restrict or prevent blocking of a light, camera, and/or any other medical instrument described herein during a procedure. The cut out may be located at a distal end or portion of the protecting feature, or the cut out can be located along an entire longitudinal length of the protecting feature thus forming a U-shaped cross section along a length thereof.

The protecting feature may include an adjuster. The adjuster may function to cause the protecting feature to move. The adjuster may function to cause the protecting feature to move distally, proximally, rotationally, or a combination thereof relative to the hand piece or patient. For example, manipulation of the adjuster may cause the cut out to be oriented in the same direction as one or more of the ports on the hand piece, in a direction away from the ports on the hand piece, or in any direction there between. For example, manipulation of the adjuster may cause the distal end of the protecting feature to move towards the distal end of the insertion tube or towards the hand piece of the medical device. This may be advantageous to properly fit a protecting feature to an insertion tube. The adjuster may function to cause a length of the protecting feature or elongated portion to change. For example, the protecting feature or elongated portion may have a length that can be adjusted (e.g., made longer or extended; made shorter or collapsed; or both), and manipulation of the adjuster may cause the length to change. Again, this may be advantageous to properly fit a protecting feature to a particular insertion tube. The adjuster may function to expand or contract a cross sectional size or diameter of the protecting feature to accommodate different size medical instruments. The adjuster may function to attach the protecting feature or sleeve to the medical device or handle so that the protecting feature or sleeve is not moveable relative to the hand piece without manipulation of the adjuster. For example, the adjuster may be threadably connected to the working channel port of the medical device, or any other portion on the medical device. Alternatively, the adjuster may be connected or attached to the hand piece via a press fit or any other suitable connection. Preferably, the connection is temporary so that the protecting feature can be separated from the medical device on demand.

FIG. 1 illustrates a medical device 10. The medical device 10 includes an insertion tube 12 and a hand piece 14. The insertion tube 12 includes a working channel 16 and a distal end 18. The hand piece 14 includes, a port 20, an eyepiece 22, and a working channel port 24. Via the working channel port 24, a medical instrument 26 can be inserted into the working channel 16 of the insertion tube 12.

FIG. 2a illustrates a cross section of the insertion tube 12 of FIG. 1 taken along line 2a-2a. A protecting feature 28 is disposed within at least a portion of a working channel 16 of the insertion tube 12. When inserted into the working channel 16 or moved within the working channel 16, the medical instrument 26 can come into contact with the protecting feature 28 rather than an inner wall or surface 48 of the working channel 16. The insertion tube 12 may include a plurality of channels 16', one or more of which may include one or more of the protecting features 28 disclosed herein. Channels 16' may be used to accommodate light fibers, optics, irrigation, suction, or the like.

FIG. 2b illustrates a cross section of the insertion tube 12 taken along line 2b-2b of FIG. 1. The protecting features 28 are located in the areas or regions around a circumference of the insertion tube 12 where the insertion tube 12 bends or deflects in order to strengthen the insertion tube 12 when the insertion tube 12. In this illustration, the insertion tube 12 is bendable or deflectable in directions identified by the double arrows 52; however, it is understood that the insertion tube 12 can be adapted to bend or deflect in arty direction. The medical instrument 26 located within the working channel 16 may come into contact the protecting features 28 when the insertion tube 12 is bent without contacting the inner walls or surfaces 48 of the insertion tube 12.

FIG. 2c illustrates a longitudinal section of the insertion tube 12 taken, along 2c-2c of FIG. 1. A protecting feature 28 is disposed within the inner wall or surface 48 of the working channel 16. In this illustration, the protecting feature 28 includes a pair of first opposing capacitors $28a1$, $28a2$, and a pair of second opposing capacitors $28b1$, $28b2$. When the medical instrument 26 is not located within the working channel 16, or when at least the distal end of the medical instrument 26 is located within the working channel 16 or is located proximal to the first capacitors $28a1$ $28a2$, a first capacitance (C1) can be measured between the first capacitors $28a1$ $28a2$ with the medical device 10 or a controller 40. Similarly, a second capacitance (C2) can be measured between the second capacitors $28b1$, $28b2$. When the medical instrument 26 is moved towards the distal end 18 of the insertion tube 12 such that at least the distal end of the medical instrument 26 is located between the first capacitors $28a1$, $28a2$, a different capacitance (C1') can be measured between the first capacitors $28a1$, $28a2$. As the medical instrument 26 is further moved towards the distal end 18 of the insertion tube 12 such that at least the distal end of the medical instrument 26 is also located between the second pair of opposing capacitors $28b1$, $28b2$, a different capacitance (C2') can be measured between the second pair of opposing capacitors $28b1$, $28b2$. The medical device 10 or controller 40 understands that when the measured capacitance between the first capacitors $28a1$, $28a2$ is C1 or C1' and the measured capacitance between the second capacitors $28b1$, $28b2$ is C2, at least a distal end of the medical instrument 26 is located proximal to the first capacitors $28a1$, $28a2$ or is located somewhere between the first and second capacitors $28a1$, $28a2$ and $28b1$, $28b2$. Accordingly, if the medical instrument 26 is a laser, for example, the medical device 10 or controller 40 may function to prevent the laser from operating or firing, thus preventing the laser wavelength fired from the laser from mechanically and/or thermally damaging the insertion tube 12. Once the medical device 10 or controller 40 measures the capacitance between the first capacitors $28a1$, $28a2$ as C1' and the capacitance between the second capacitors $28b$, $28b2$ as C2', the medical device 10 and/or controller 40 understands that at least the distal end of the medical instrument 26 is located distal to the second capacitors $28b1$, $28b2$ and is thus at or near the distal end 18 of the insertion tube 12. Accordingly, if the medical instrument 26 is a laser, the laser can be safely operated or fired with minimized risk that the laser wavelength will contact the inner portion of the insertion tube 12.

Figure 2D:
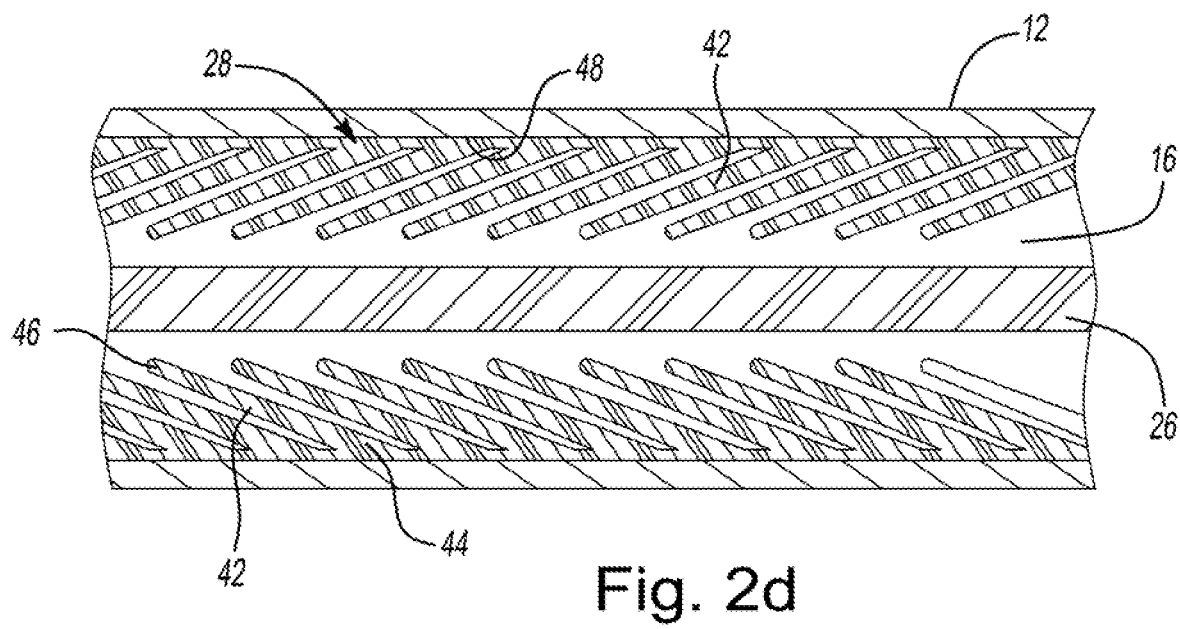
FIG. 2d is a cross-sectional view of an insertion tube of FIG. 1.

FIG. 2d illustrates a longitudinal section of the insertion tube 12 of FIG. 1 taken along line 2d-2d of FIG. 1. A protecting feature 28 comprising a series of protecting segments 42 extends form an inner wall or surface 48 of the working channel 16 and/or insertion tube 12. The protecting segments 42 may be akin to snake skin or roof shingles, where a first portion 44 of each segment 42 is attached to an interior of the working channel 16 or to an adjacent segment 42, while a second portion 46 of each segment 42 is moveable and free of attachment. When inserted into the working channel 16 or moved within the working channel 16, the medical instrument 26 can come into contact with the protecting feature 28 rather than an inner wall or surface of the working insertion tube 12.

FIG. 3 illustrates a protecting feature 28. In this illustration, the protecting feature 28 may be a sleeve. The protecting feature 28 includes an elongated portion 30 that extends between a distal end 32 and a proximal end 34. In this illustration, the elongated portion 30 includes a cut out 36; however, it is understood that the elongated portion 30 can be free of cut outs and thus have a continuous cross section in other illustrations. The proximal end 34 of the protecting feature 28 includes an adjuster 38. The protecting feature 28 is inheritable into the working channel 16 of the insertion tube 12 illustrated in FIG. 1. During use, a medical instrument 26 can be inserted into the working channel 12 and instead of contacting an inner portion or wall of the working channel 16, the medical instatement 26 can instead contact the elongated portion 30 of the protecting feature 28. The distal end 32 of the sleeve 30 can be aligned with the distal end 18 of the insertion tube 12 or the distal end 32 can be positioned at a desired location somewhere between the distal end 18 of the insertion tube 12 and the working channel port 24. The adjuster 38 can function to connect the protecting feature 28 to the medical device 10. Manipulation of the adjuster 36 can cause a location of the protecting feature 28 within the insertion tube 16 to move, rotate, or both; can cause a length of the elongated portion 30 to change (e.g., expand or contract), or a combination thereof.

Figure 5:
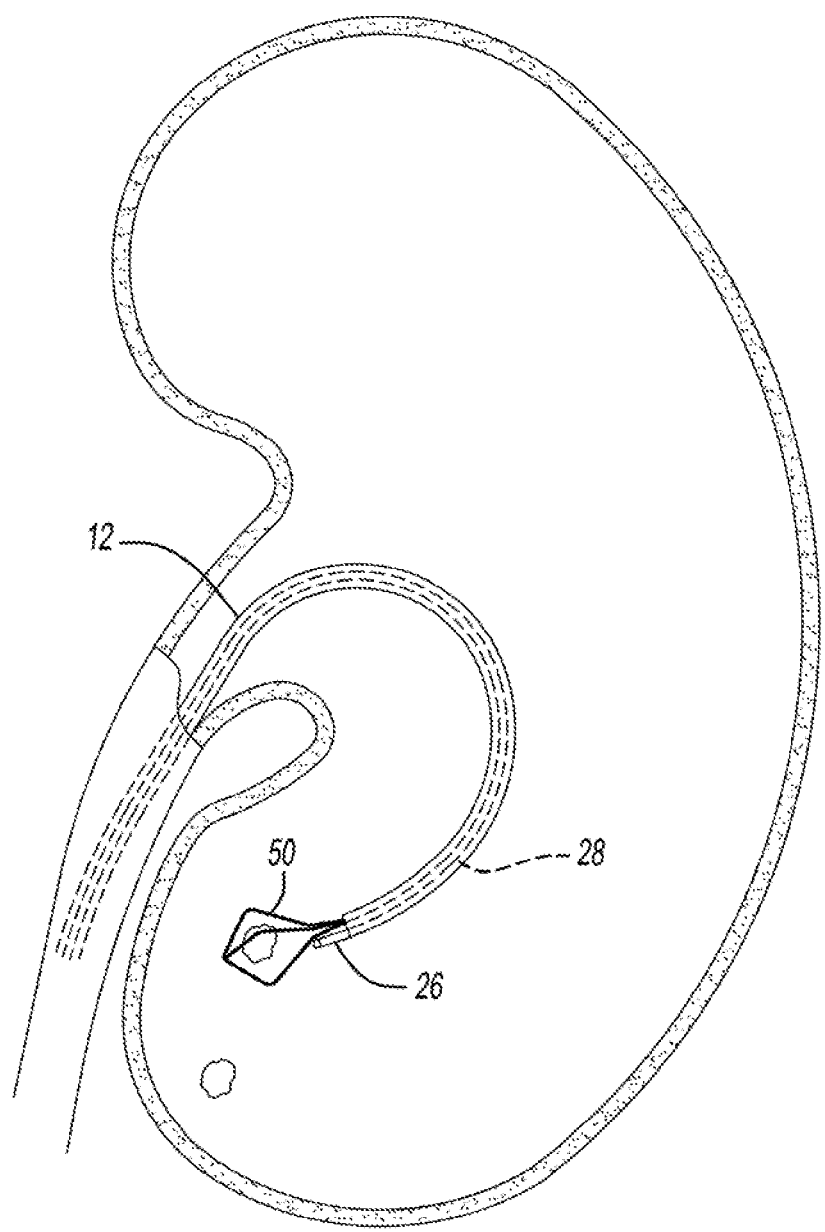
FIG. 5 is a cross-sectional view of an insertion tube and medical instrument in a site of interest.

FIG. 4 illustrates a medical device 10 including the protecting feature 28 of FIG. 3. By manipulating the adjuster 36, a position of the sleeve 30 and/or the distal end 32 of the sleeve 30 can be repositioned in the insertion tube 12. FIG. 4 illustrates an end of the medical instrument 26 extending beyond a distal end 18 of the insertion tube 12, which may make it desirable to have a protecting feature 28 whose length and/or position can be adjusted. The medical device 10 can include a stopper 52 that may function to support the sleeve 30 from moving within the insertion tube 12 following insertion. FIG. 5 illustrates a cross sectional-view of an insertion tube 12 and medical instrument 26 accessing a site of interest 50, which in this example is a lower pole of a kidney. The insertion tube 12 is illustrated in a bent position to access the site of interest 50. The insertion tube 12 includes one or more protecting features 28 disclosed herein.

The invention claimed is:

1. An endoscope comprising:
a controller;
an insertion tube;
a working channel within the insertion tube; and
a protecting feature disposed within at least a portion of the working channel, the protecting feature adapted to protect the working channel from thermal damage and/or from mechanical damage caused by a medical instrument in the working channel;
wherein the protecting feature includes a first pair of opposing parallel plate capacitors operably coupled to the controller and a second pair of opposing parallel plate capacitors operably coupled to the controller;
wherein during use:
a change in capacitance between the first pair of opposing parallel plate capacitors is indicative of the medical instrument being located in the working channel; and
a change in capacitance between the second pair of opposing parallel plate capacitors is indicative of the medical instrument being located in the working channel and at a location within the working channel that is suitable for the medical instrument to be operated; and
wherein the controller is operable such that when the change in the capacitance between the first pair of opposing parallel plate capacitors is detected without the change in the capacitance between the second pair of opposing parallel plate capacitors also being detected, the controller prevents operation of the medical instrument.

2. The endoscope of claim 1, wherein the protecting feature is located at a distal end of the working channel.

3. The endoscope of claim 1, wherein the protecting feature is located along an entire length of the working channel.

4. The endoscope of claim 1, wherein the protecting feature comprises one or more protecting segments, and each of the one or more protecting segments include a first end and a second end, the first end is connected to the working channel or to an adjacent protecting segment, and the second end is free of any connections.

5. The endoscope of claim 1, wherein a distal end of the protecting feature includes a cut out to prevent the protecting feature from blocking a light, a camera, and/or the medical instrument inserted into the working channel.

6. The endoscope of claim 1, wherein the protecting feature includes a U-shaped cross section extending along an entire length of the working channel, the U-shaped cross section prevents the protecting feature from blocking a light, a camera, and/or the medical instrument that is inserted into the working channel.

7. The endoscope of claim 1, wherein the protecting feature is separable from the working channel so that the protecting feature can be cleaned or disposed of after use.

8. The endoscope of claim 1, wherein the protecting feature is adjustable so that a position of the protecting feature relative to a distal end of the insertion tube is changeable.

9. The endoscope of claim 1, wherein a length of the protecting feature is adjustable such that the length of the protecting feature can be expanded or contracted.

10. The endoscope of claim 1, wherein the protecting feature is fixedly connected to the working channel.

11. The endoscope of claim 1, wherein the protecting feature includes a material having high thermal conductivity in the range of 1 to 20 W/mK.

12. The endoscope of claim 1, wherein the medical instrument is a laser.

13. The endoscope of claim 1, wherein a distal end of the protecting feature includes a cut out.

14. The endoscope of claim 1, wherein the protecting feature includes a U-shaped cross section.

15. The endoscope of claim 1, wherein the protecting feature is adjustable.

16. A method of protecting a working channel located within an insertion tube of an endoscope, the method comprising:
- determining a first capacitance between a first pair of opposing parallel plate capacitors;
- determining a first capacitance between a second pair of opposing parallel plate capacitors;
- monitoring the first capacitance and the second capacitance, and either:
- allowing a laser located within the working channel to operate when there is a change to both the first capacitance and the second capacitance, wherein the change to both the first capacitance and the second capacitance is indicative that the laser is located at a distal end of the insertion tube, or
- restricting the laser from operating when there is no change to one or both of the first capacitance and the second capacitance, wherein no change to one or both the first capacitance and the second capacitance is indicative that the laser is located proximal to the distal end of the insertion tube.

17. An endoscope comprising:
- a controller;
- an insertion tube extending along a longitudinal axis;
- a working channel within the insertion tube; and
- a protecting feature disposed within at least a portion of the working channel, the protecting feature adapted to protect the working channel from thermal damage and/or from mechanical damage caused by a medical instrument in the working channel;
- wherein the protecting feature includes a first pair of opposing parallel plate capacitors operably coupled to the controller and a second pair of opposing parallel plate capacitors operably coupled to the controller and longitudinally spaced from the first pair of opposing parallel plate capacitors;
- wherein the controller is operable such that when a change in capacitance between the first pair of opposing parallel plate capacitors is detected without a change in capacitance between the second pair of opposing parallel plate capacitors also being detected, the controller prevents operation of the medical instrument.

18. The endoscope of claim 17, wherein the medical instrument is a laser.

19. The endoscope of claim 17, wherein the protecting feature is located at a distal end of the working channel.

20. The endoscope of claim 17, wherein the protecting feature is fixedly connected to the working channel.

* * * * *